United States Patent
Ishizuka et al.

(10) Patent No.: US 10,560,658 B2
(45) Date of Patent: Feb. 11, 2020

(54) IMAGING MODULE AND IMAGING-MODULE-ATTACHED CATHETER

(71) Applicant: FUJIKURA LTD., Tokyo (JP)

(72) Inventors: Takeshi Ishizuka, Sakura (JP); Kenichi Ishibashi, Sakura (JP); Shingo Ishii, Tokyo (JP); Daisuke Murakami, Sakura (JP); Yoshinobu Numasawa, Sakura (JP); Hideaki Usuda, Tokyo (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 16/115,665

(22) Filed: Aug. 29, 2018

(65) Prior Publication Data

US 2019/0068917 A1 Feb. 28, 2019

(30) Foreign Application Priority Data

Aug. 31, 2017 (JP) ................. 2017-167992

(51) Int. Cl.
*H04N 7/00* (2011.01)
*H04N 7/10* (2006.01)
(Continued)

(52) U.S. Cl.
CPC ............. *H04N 7/10* (2013.01); *H01R 12/53* (2013.01); *H04N 5/2251* (2013.01); *H05K 1/11* (2013.01);
(Continued)

(58) Field of Classification Search
CPC ....... A61B 1/00101; A61B 1/05; A61B 1/051; H04N 7/10; H04N 5/2251; H01R 12/53;
(Continued)

(56) References Cited

U.S. PATENT DOCUMENTS 6,086,528 A * 7/2000 Adair ................. A61B 1/00082
600/104
2006/0025651 A1 2/2006 Adler et al.
(Continued)

FOREIGN PATENT DOCUMENTS

EP 3206386 A1 8/2017
JP H07100101 A 4/1995
(Continued)

OTHER PUBLICATIONS

Shiraishi. "JPH10-99267A Translation". (Year: 1998).*
(Continued)

*Primary Examiner* — Zhihan Zhou
(74) *Attorney, Agent, or Firm* — Osha Liang LLP

(57) ABSTRACT

An imaging module includes: an image-sensing device; a first substrate including a first insulating substrate main body that includes a plurality of surfaces, an electrode terminal, a first cable terminal disposed on only one of the plurality of surfaces of the first insulating substrate main body; a second substrate including a second insulating substrate main body and a second cable terminal; and a signal cable disposed between the first substrate and the second substrate, that electrically connects the first cable terminal to the second cable terminal. The one of the plurality of surfaces of the first insulating substrate main body where the first cable terminal is connected to the signal cable and a surface of the second insulating substrate main body where the second cable terminal is connected to the signal cable are disposed on a same plane.

6 Claims, 4 Drawing Sheets

(51) Int. Cl.
  *H01R 12/53*    (2011.01)
  *H05K 1/18*     (2006.01)
  *H04N 5/225*    (2006.01)
  *H05K 1/11*     (2006.01)

(52) U.S. Cl.
  CPC ... *H05K 1/181* (2013.01); *H05K 2201/10121* (2013.01); *H05K 2201/10151* (2013.01); *H05K 2201/10189* (2013.01)

(58) Field of Classification Search
  CPC .......... H05K 1/11; H05K 2201/10151; H05K 2201/10189; H05K 2201/10121; H05K 1/181
  See application file for complete search history.

(56) References Cited

U.S. PATENT DOCUMENTS

| | | | |
|---|---|---|---|
| 2006/0069311 A1* | 3/2006 | Sullivan | A61B 1/0052 600/149 |
| 2008/0214892 A1 | 9/2008 | Irion et al. | |
| 2013/0269434 A1* | 10/2013 | Kamisuki | G01P 15/125 73/514.32 |
| 2014/0121526 A1* | 5/2014 | Matsumoto | A61B 8/12 600/459 |
| 2015/0378144 A1* | 12/2015 | Handte | H04N 5/2251 250/208.1 |
| 2018/0006388 A1* | 1/2018 | Yamada | H01R 9/05 |

FOREIGN PATENT DOCUMENTS

| | | | |
|---|---|---|---|
| JP | H10-099267 A | 4/1998 | |
| JP | H10-99267 A | 4/1998 | |
| JP | 2006-109097 A | 4/2006 | |
| JP | 2010-258582 A | 11/2010 | |
| JP | 2015-173736 A | 10/2015 | |
| JP | 2017140426 A | 8/2017 | |
| WO | WO-2016151762 A1 * | 9/2016 | ............... H01R 9/05 |

OTHER PUBLICATIONS

Extended European Search Report in counterpart European Application No. 18190621.5 dated Jan. 2, 2019 (7 pages).

Notice of Reasons for Refusal issued in corresponding Japanese Patent Application 2017-167992, dated May 21, 2019, with translation (10 pages).

* cited by examiner

IMAGING MODULE AND IMAGING-MODULE-ATTACHED CATHETER

CROSS REFERENCE TO RELATED APPLICATIONS

This application claims priority from Japanese Patent Application No. 2017-167992 filed on Aug. 31, 2017, the contents of which are incorporated herein by reference in their entirety.

BACKGROUND

Field of the Invention

The present invention relates to an imaging module and an imaging-module-attached catheter.

Description of the Related Art

An imaging module having a configuration in which a solid-state image sensing device (hereinbelow, may be simply referred to as an image-sensing device) is electrically connected to an end of an electrical cable with a wiring substrate interposed therebetween is often employed in electronic endoscopes (for example, Japanese Unexamined Patent Application, First Publication No. 2006-109097).

In this kind of imaging module, a plurality of ends of the electrical cable are electrically connected to wiring of the wiring substrate, and each electrical cable is electrically connected to the image-sensing device via the wiring of the wiring substrate.

In an imaging device such as an endoscope using the aforementioned imaging module, a configuration is often employed in which a plurality of electrical cables connected to an imaging module and a wiring substrate of the imaging module are accommodated in a tube. Furthermore, an back end that is opposite to the imaging module side of the electrical cable of this imaging device is drawn from the tube and is electrically connected to an image information processing device that receives imaging signals from the electrical cable and displays an image on a display device such as a monitor.

In recent years, it has been studied that an imaging module is applied to a medical instrument such as a catheter that is provided with a lumen or a working channel. However, in the case of applying the imaging module having the aforementioned configuration to a medical instrument, it is necessary to increase a diameter of the medical instrument, and it is difficult to achieve a reduction in diameter which is required for the medical instrument.

SUMMARY

One or more embodiments of the invention provide an imaging module which is applicable to a medical instrument that is provided with a channel such as lumen and has a small-diameter.

An imaging module according to one or more embodiments of the invention includes: an image-sensing device including an image-sensing device electrode; a first substrate including a first substrate main body serving as an insulating member, a first wiring formed on the first substrate main body, an electrode terminal electrically connected to the image-sensing device electrode and the first wiring, a first cable terminal that is formed only on one of the surfaces of the first substrate main body and is electrically connected to the first wiring, the first substrate having an end face connected to the image-sensing device; a second substrate including a second substrate main body serving as an insulating member, a second wiring formed on the second substrate main body, and a second cable terminal that is formed only on one of the surfaces of the second substrate main body and is electrically connected to the second wiring; and a signal cable that is provided between the first substrate and the second substrate and electrically connects the first cable terminal to the second cable terminal, wherein a surface on which the first cable terminal is connected to the signal cable and a surface on which the second cable terminal is connected to the signal cable are located on the same plane.

In the imaging module according to one or more embodiments of the invention, the image-sensing device may have an electrode surface on which the image-sensing device electrode is provided, and the first substrate may be connected to the electrode surface so that an end face of the first substrate main body is located between two image-sensing device electrodes.

In the imaging module according to one or more embodiments of the invention, the first substrate may have a first surface, a second surface opposite to the first surface, and a through electrode that penetrates through the first substrate main body between the first surface and the second surface, and the first wiring may be formed on the first surface and the second surface and is electrically connected to the through electrode.

In the imaging module according to one or more embodiments of the invention, the signal cable may be a coaxial cable.

An imaging-module-attached catheter according to one or more embodiments of the invention includes: the imaging module according to one or more embodiments; and a tube including: a module arrangement region in which the first substrate and part of the signal cable are arranged; and a channel that is located between the first cable terminal and the second cable terminal and is next to the module arrangement region, wherein as seen from the image-sensing device, the channel is disposed within an outline of the image-sensing device on a plane of projection.

As described above, according to one or more embodiments of the invention, it is possible to provide an imaging module which is applicable to a medical instrument that is provided with a channel such as lumen and has a small-diameter. Additionally, it is possible to provide a catheter including both a channel and an imaging module and having a small diameter.

DETAILED DESCRIPTION

Figure 1:
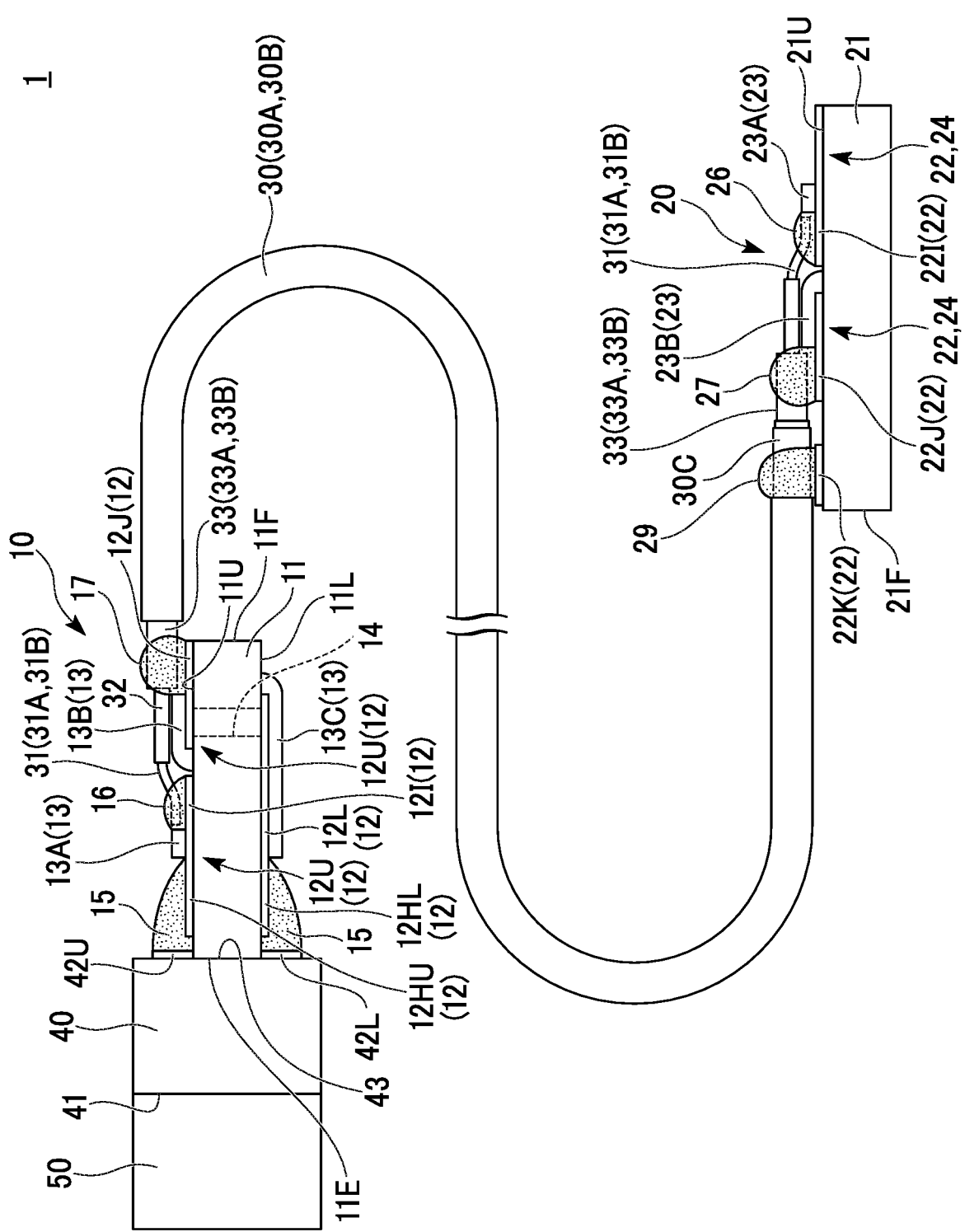
FIG. 1 is a partial cross-sectional view showing a schematic configuration of an imaging module according to one or more embodiments of the invention.

Hereinafter, embodiments of the invention will be described with reference to drawings.

In the drawings showing embodiments of the invention, in order for the respective components to be of understandable size in the drawings, the dimensions and the proportions of the components are modified as needed compared with the real components.

FIG. 1 is a partial cross-sectional view showing a schematic configuration of the imaging module 1 according to one or more embodiments of the invention.

The imaging module 1 includes a first substrate 10, a second substrate 20, a signal cable 30, a solid-state image sensing device 40 (image-sensing device), and a lens housing 50.
(First Substrate 10)

The first substrate 10 includes a first substrate main body 11 serving as an insulating member and a first wiring 12 (upper face wiring 12U, and lower face wiring 12L) formed on the first substrate main body 11. The first substrate main body 11 has an upper face 11U (first surface) and a lower face 11L (second surface) opposite to the upper face 11U. The upper face wiring 12U is formed on the upper face 11U. The lower face wiring 12L is formed on the lower face 11L. The first wiring 12 has a conductive wiring pattern formed on both the upper face 11U and the lower face 11L.

The first substrate main body 11 (first substrate 10) has an outer end face 11E (end face) connected to the solid-state image sensing device 40 and an inner end face 11F opposite to the outer end face 11E. In a state where the outer end face 11E is connected to the solid-state image sensing device 40, the first substrate main body 11 extends in a direction substantially orthogonal to an electrode surface 43 of the solid-state image sensing device 40. The inner end face 11F is exposed to a space adjacent to the signal cable 30.

The first substrate 10 includes a through electrode 14 that penetrates through the first substrate main body 11 between the upper face 11U and the lower face 11L. The through electrode 14 electrically connects the upper face wiring 12U to the lower face wiring 12L.

An electrode terminal 12HU that is electrically connected to the upper face wiring 12U is formed on the upper face 11U. An electrode terminal 12HL that is electrically connected to the lower face wiring 12L is formed on the lower face 11L. That is, electrode terminals are formed on both the upper face 11U and the lower face 11L. The electrode terminal 12HU is electrically connected via solder 15 to an image-sensing device electrode 42U (42) of the solid-state image sensing device 40 which will be described later. The electrode terminal 12HL is electrically connected to an image-sensing device electrode 42L (42) of the solid-state image sensing device 40 via the solder 15.

A center conductor terminal 12I (first cable terminal) and an external conductor terminal 12J (first cable terminal) are formed only on one of the surfaces of the first substrate main body 11, that is, only on the upper face 11U. The center conductor terminal 12I and the external conductor terminal 12J are electrically connected to the upper face wiring 12U. The center conductor terminal 12I is electrically connected via solder 16 to a center conductor 31 of the signal cable 30 which will be described later. The external conductor terminal 12J is electrically connected via solder 17 to an external conductor 33 of the signal cable 30.

Upper face resists 13A and 13B (13) are formed on the upper face 11U of the first substrate main body 11 so as to coat a surface of the upper face wiring 12U. The upper face resist 13A is formed between the solder 15 and the solder 16. The upper face resist 13B is formed between the solder 16 and the solder 17. A lower face resist 13C (13) is formed on the lower face 11L of the first substrate main body 11 so as to coat a surface of the lower face wiring 12L.

In FIG. 1, as seen in the direction from the solid-state image sensing device 40 toward the inner end face 11F, the signal cable 30 is disposed within an outline of the solid-state image sensing device 40 on a plane of projection, and the signal cable 30 does not partially protrude from the outline of the solid-state image sensing device 40 shown in the plane of projection of the solid-state image sensing device 40.
(Second Substrate 20)

The second substrate 20 includes a second substrate main body 21 serving as an insulating member and a second wiring 22 formed on the second substrate main body 21. The second substrate main body 21 has an upper face 21U (one of the surfaces). A center conductor terminal 22I (second cable terminal), an external conductor terminal 22J (second cable terminal), and a shield terminal 22K (second cable terminal) are formed on the upper face 21U. The center conductor terminal 22I and the external conductor terminal 22J are electrically connected to the second wiring 22.

The center conductor terminal 22I is electrically connected via solder 26 to the center conductor 31 of the signal cable 30. The external conductor terminal 22J is electrically connected via solder 27 to the external conductor 33 of the signal cable 30. The shield terminal 22K is electrically connected via solder 29 to a shield conductor 30C of the signal cable 30.

Resists 23A and 23B (23) are formed on the upper face 21U of the second substrate main body 21 so as to coat a surface of the second wiring 22. The resist 23B is formed between the solder 26 and the solder 27. The resist 23A is formed close to the solder 26 on the center conductor terminal 22I.

The second substrate 20 includes an external connection terminal 24 formed on the second substrate main body 21, and the external connection terminal 24 is electrically connected to the second wiring 22. The external connection terminal 24 is connected to an external device. Note that, the external connection terminal 24 and the second wiring 22 are simultaneously formed on the second substrate main body 21.
(Solid-State Image Sensing Device 40 and Lens Housing 50)

The solid-state image sensing device 40 includes a light-receiving face 41, an electrode surface 43 located on the opposite side of the light-receiving face 41, and the image-sensing device electrodes 42U and 42L (two image-sensing device electrodes) provided on the electrode surface 43. The first substrate 10 is connected to the electrode surface 43 so that the outer end face 11E of the first substrate main body 11 is located between the image-sensing device electrodes 42U and 42L.

In a state where the outer end face 11E of the first substrate 10 is connected to the electrode surface 43 of the solid-state image sensing device 40, the image-sensing device electrode 42U has a surface parallel to the direction substantially orthogonal to the electrode terminal 12HU, and the image-sensing device electrode 42L has a surface parallel to the direction substantially orthogonal to the electrode terminal 12HL. In this configuration, the solder 15 connects the image-sensing device electrode 42U and the electrode terminal 12HU which are substantially orthogonal to each other, and connects the image-sensing device electrode 42L and the electrode terminal 12HL which are substantially orthogonal to each other.

FIG. 1 shows the image-sensing device electrodes 42U and 42L which are arranged at the upper position and the lower position, respectively; however, when seen in a plan view of the electrode surface 43 (in a plan view showing the electrode surface 43 when viewed in a vertical direction) four image-sensing device electrodes 42 are arranged on the electrode surface 43. That is, two image-sensing device electrodes 42U and two image-sensing device electrodes 42L are formed on the electrode surface 43.

The lens housing 50 is connected to the light-receiving face 41, and a lens unit such as an object lens is mounted on the lens housing 50. As the solid-state image sensing device 40, for example, a CMOS (complementary metal oxide semiconductor) is preferably used.

(Signal Cable 30)

Figure 2:
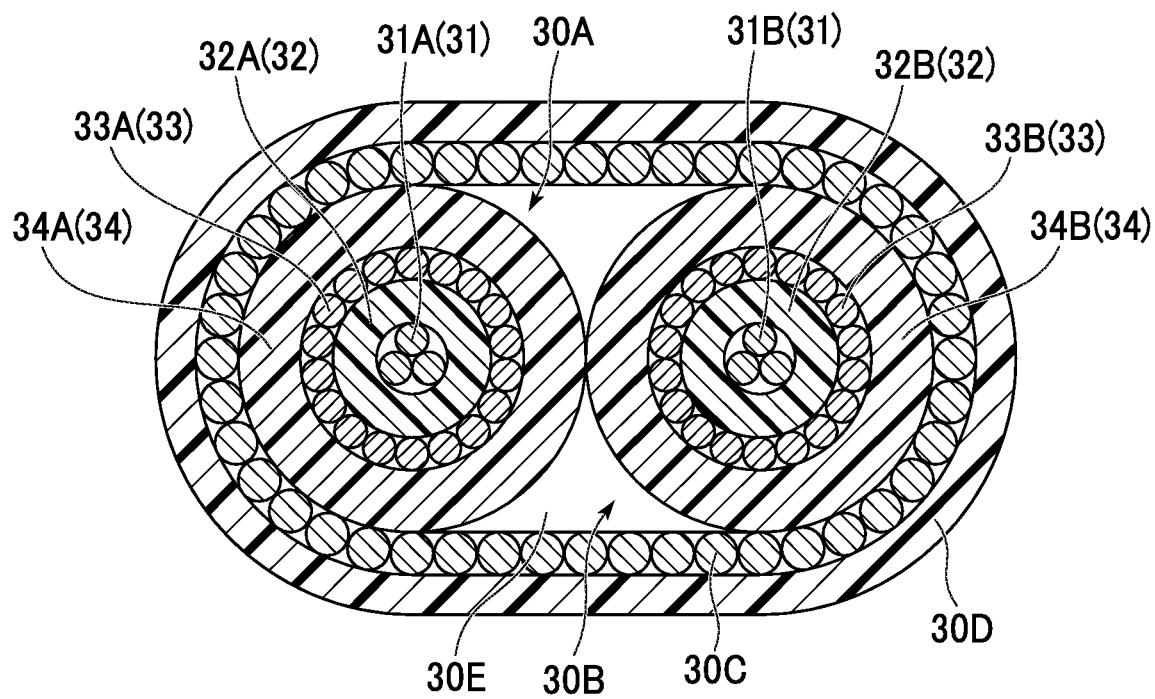
FIG. 2 is a cross-sectional view showing a signal cable of the imaging module according to one or more embodiments of the invention.

FIG. 2 is a cross-sectional view showing the signal cable 30 of the imaging module according to one or more embodiments of the invention.

The signal cable 30 is provided between the first substrate 10 and the second substrate 20 and includes two coaxial cable (signal line, a first coaxial cable 30A, a second coaxial cable 30B), a shield conductor 30C that surrounds the first coaxial cable 30A and the second coaxial cable 30B, and an outer coating 30D that surrounds the shield conductor 30C. The shield conductor 30C is provided on the entire inner peripheral surface of the outer coating 30D and is formed in a layer shape.

In FIG. 2, for example, the structure is shown in which the shield conductor 30C is disposed separately from a cable contact portion at which the side portions of the first coaxial cable 30A and the second coaxial cable 30B are in contact with each other, and a space 30E is present between the cable contact portion and the shield conductor 30C located at both sides of the cable contact portion. However, as a cross-sectional structure of the signal cable 30, a cross-sectional structure is applicable, in which the shield conductor 30C enters a region of the space 30E shown in FIG. 2 and a space is substantially absent among the first coaxial cable 30A, the second coaxial cable 30B, and the layer-shaped shield conductor 30C.

Each of the coaxial cables 30A and 30B includes a center conductor 31 (31A, 31B), an internal insulator 32 (32A, 32B), an external conductor 33 (33A, 33B), and an external insulator 34 (34A, 34B). For example, the center conductor 31 is used as a signal line that supplies a signal to the solid-state image sensing device 40, and the external conductor 33 is used as a power supply line that supplies electric power to the solid-state image sensing device 40.

The center conductor 31 (31A, 31B) electrically connects the center conductor terminal 12I of the first substrate 10 to the center conductor terminal 22I of the second substrate 20.

The external conductor 33 (33A, 33B) electrically connects the external conductor terminal 12J of the first substrate 10 to the external conductor terminal 22J of the second substrate 20.

The shield conductor 30C and the outer coating 30D surrounds the first coaxial cable 30A and the second coaxial cable 30B over the entire signal cable 30. The shield conductor 30C and the outer coating 30D are removed at the position close to the first substrate 10 (the position close to the inner end face 11F shown in FIG. 1), and the first coaxial cable 30A and the second coaxial cable 30B are exposed. On the other hand, the outer coating 30D is removed at the position close to the second substrate 20 (the position close to the inner end face 21F shown in FIG. 1), and the shield conductor 30C is exposed, and the shield conductor 30C is electrically connected to the shield terminal 22K via the solder 29. In this configuration, the shield terminal is connected to, for example, GND, and therefore the shield conductor 30C is grounded.

Furthermore, as shown in FIG. 1, the external conductor 33 and the center conductor 31 which constitute each of the first coaxial cable 30A and the second coaxial cable 30B are exposed so as to correspond to wiring patterns of the first substrate 10 and the second substrate 20. Specifically, between the solder 27 and the solder 29, the external conductor 33 (33A, 33B) is exposed from the external insulator 34 (34A, 34B). The exposed external conductor 33 (33A, 33B) is electrically connected to the external conductor terminal 22J via the solder 27. Between the solder 27 and the solder 26, the center conductor 31 (31A, 31B) is exposed from the internal insulator 32 (32A, 32B). The exposed center conductor 31 (31A, 31B) is electrically connected to the center conductor terminal 22I via the solder 26.

(Positional Relationship Among First Substrate 10, Second Substrate 20, and Signal Cable 30)

Figure 3:
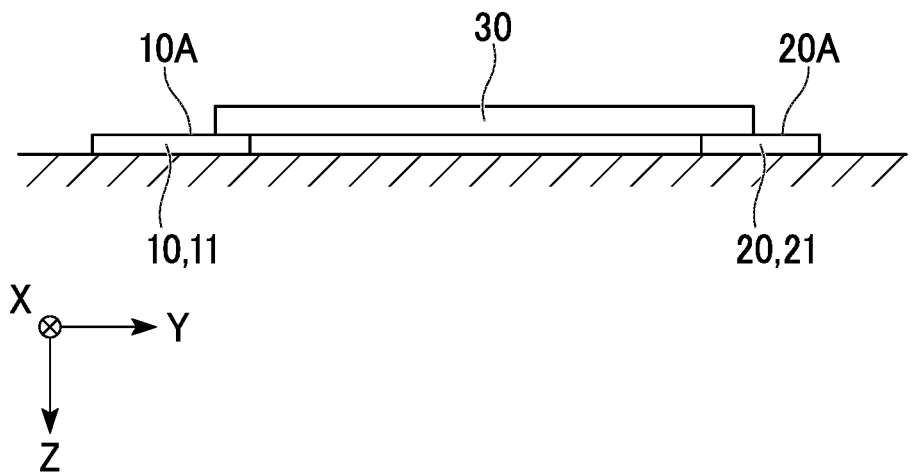
FIG. 3 is a view showing a schematic configuration of the imaging module according to one or more embodiments of the invention and is an explanatory view showing a positional relationship among a first substrate, a second substrate, and a signal cable.

FIG. 3 is a view showing a schematic configuration of the imaging module according to one or more embodiments of the invention and is an explanatory view showing a positional relationship among the first substrate 10, the second substrate 20, and the signal cable 30.

As shown in FIG. 3, in a state where the first substrate 10 and the second substrate 20 are on the same horizontal plane, the surface 10A (upper face 11U, first surface) on which the first cable terminal is connected to the signal cable 30 and the surface 20A (upper face 21U) on which the second cable terminal is connected to the signal cable 30 are located on the same plane. Furthermore, the first substrate 10 is connected to the second substrate 20 with the signal cable 30 interposed therebetween so that one signal cable 30 corresponds to a pair of the first substrate 10 and the second substrate 20.

In the imaging module 1, in a state where the signal cable 30 extends straight without torsional deformation, the surface 10A on which the center conductor terminal 12I and the external conductor terminal 12J of the first substrate 10 are formed is referred to as an upper face, a surface opposite to the surface 10A is referred to as a lower face, the surface 20A on which the center conductor terminal 22I and the external conductor terminal 22J of the second substrate 20 are formed is referred to as an upper face, and a surface opposite to the surface 20A is referred to as a lower face.

Accordingly, as shown in FIG. 3, in a state where the lower face of each of the first substrate 10 and the second substrate 20 are in contact with the same horizontal plane, the first substrate 10 and the second substrate 20 can be mounted on the same horizontal plane. As shown in FIG. 3, when the lower faces of the first substrate 10 and the second substrate 20 are in contact with the same horizontal plane and are mounted on the same horizontal plane, the signal cable 30 is located at the upper side of the first substrate 10 and the second substrate 20.

In this configuration, in a state where the first substrate main body 11 constituting the first substrate 10 and the second substrate main body 21 constituting the second substrate 20 are fixed on the same horizontal plane, the signal cable 30 can be connected to each of the surfaces 10A and 20A by soldering, and it is possible to simplify a step of manufacturing the imaging module 1.

Furthermore, in order to effectively mass-produce the imaging module 1, regarding a plurality of pairs of the first substrate 10 and the second substrate 20 and a plurality of signal cables 30, it is necessary to collectively connect the pairs of the first substrate 10 and the second substrate 20 to the plurality of the signal cables 30 by soldering so that one signal cable 30 corresponds to each pair of the first substrate 10 and the second substrate 20.

In this case, in a state where the surface 10A of the first substrate 10 and the surface 20A of the second substrate 20 are located on the same plane and in a state where the plurality of pairs of the first substrate 10 and the second substrate 20 are arranged to align in the X-direction (in a direction vertical to the paperface shown in FIG. 3), it is possible to collectively connect the plurality of the signal cables 30 to the plurality of pairs of the first substrate 10 and the second substrate 20.

In the above-described connection step, since the surface 10A of the first substrate 10 and the surface 20A of the second substrate 20 are arranged on the same plane, it is possible to supply solder to the surfaces 10A and 20A so as to be directed in the Z-direction (direction of gravitational force), and it is thereby possible to increase the manufacturing efficiency in the mass production line of the imaging module 1.

As a result of arranging the surface 10A of the first substrate 10 and the surface 20A of the second substrate 20 on the same plane, it is not necessary to flip the first substrate 10 or the second substrate 20, and also it is not necessary to supply solder to a back surface of the substrate (in the direction opposite to the direction of gravitational force, in the direction that is indicated by the arrow and is opposite to the Z-direction). Accordingly, it is possible to achieve both mass production and simplification of production step of the imaging module 1.

Note that, not only in the case of collectively connecting the plurality of pairs of the first substrate 10 and the second substrate 20 to the plurality of the signal cables 30 by soldering, but also in the case of sequentially connecting the signal cable 30 to each of the pairs of the first substrate 10 and the second substrate 20, it is not necessary to flip the first substrate 10 or the second substrate 20, and it is possible to increase the manufacturing efficiency in the mass production line of the imaging module 1.

(Wiring Pattern on First Substrate 10)

FIGS. 4A and 4B are views each showing a wiring pattern formed on the first substrate of the imaging module according to one or more embodiments of the invention. FIG. 4A shows a wiring pattern of the upper face wiring 12U formed on the upper face 11U of the first substrate main body 11. FIG. 4B shows a wiring pattern of the lower face wiring 12L formed on the lower face 11L of the first substrate main body 11. FIG. 4B is not a bottom view showing the lower face 11L but is a projection view as seen from the upper face 11U shown in FIG. 4A. Consequently, the broken line part shown in FIG. 4A corresponds to the solid line part shown in FIG. 4B.

Figure 4:
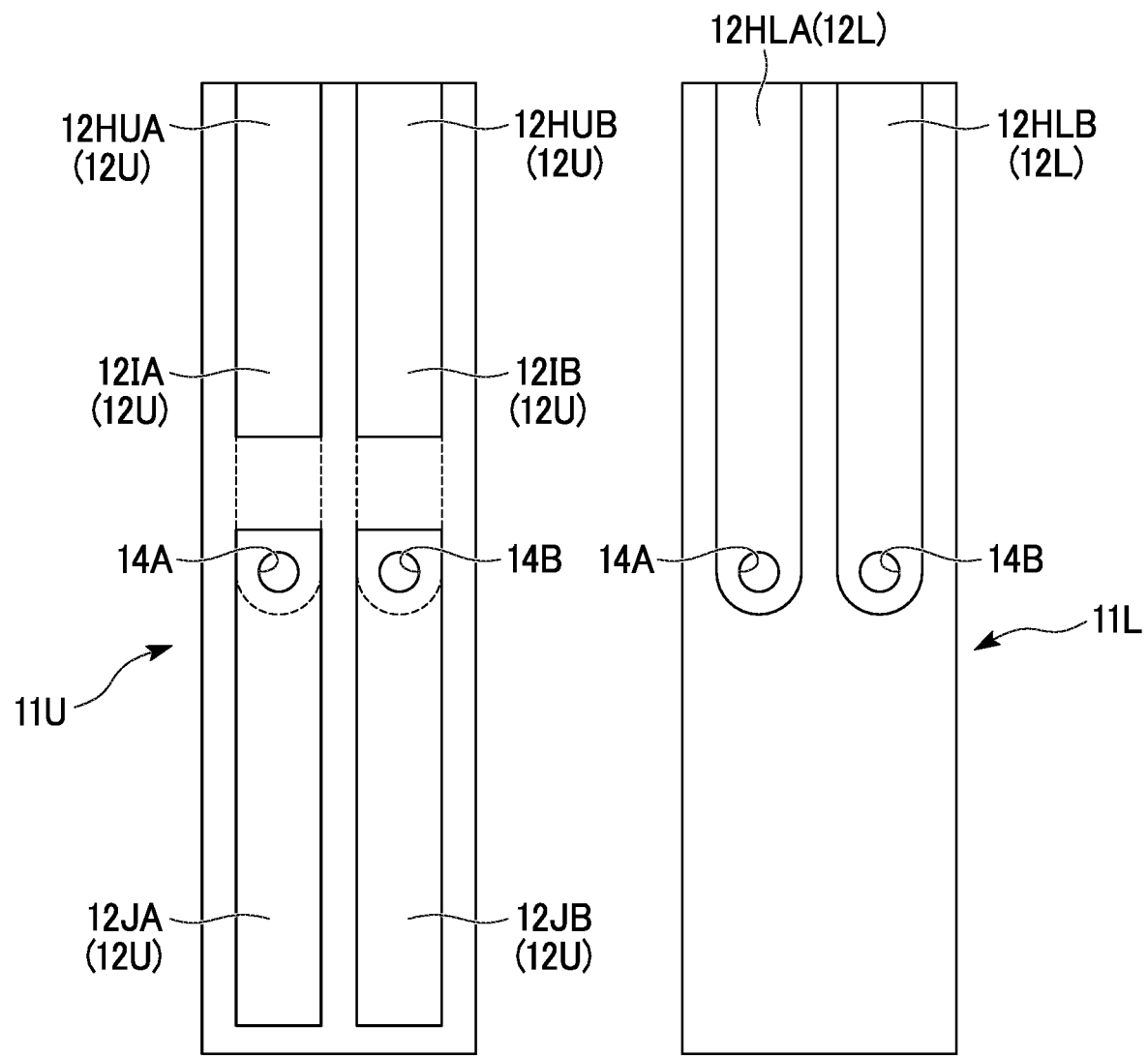
FIG. 4A is a plan view showing a wiring pattern formed on the first substrate of the imaging module according to one or more embodiments of the invention and is an explanatory view showing a connection structure between the image-sensing device and the signal cable.
FIG. 4B is a plan view showing a wiring pattern formed on the first substrate of the imaging module according to one or more embodiments of the invention and is an explanatory view showing a connection structure between the image-sensing device and the signal cable.

Note that, as shown in FIG. 1, the upper face resists 13A and 13B and the lower face resist 13C are formed on the upper face 11U and the lower face 11L of the first substrate main body 11; however, in FIG. 4, the resists 13A, 13B, and 13C are omitted.

Reference numeral 12JA corresponds to the external conductor terminal 12J and is a terminal connected to the external conductor 33A of the first coaxial cable 30A via the solder 17. Hereinbelow, it will be referred to as an external conductor terminal 12JA. Reference numeral 12JB corresponds to the external conductor terminal 12J, and is a terminal connected to the external conductor 33B of the second coaxial cable 30B via the solder 17. Hereinbelow, it will be referred to as an external conductor terminal 12JB.

Reference numeral 12IA corresponds to the center conductor terminal 12I and is a terminal connected to the center conductor 31A of the first coaxial cable 30A via the solder 16. Hereinbelow, it will be referred to as a center conductor terminal 12IA. Reference numeral 12IB corresponds to the center conductor terminal 12I and is a terminal connected to the center conductor 31B of the second coaxial cable 30B via the solder 16. Hereinbelow, it will be referred to as a center conductor terminal 12IB.

Reference numeral 12HUA is a terminal corresponding to the electrode terminal 12HU and hereinbelow will be referred to as an electrode terminal 12HUA. Reference numeral 12HUB is a terminal corresponding to the electrode terminal 12HU and hereinbelow will be referred to as an electrode terminal 12HUB.

Reference numeral 12HLA is a terminal corresponding to the electrode terminal 12HL and hereinbelow will be referred to as an electrode terminal 12HLA. Reference numeral 12HLB is a terminal corresponding to the electrode terminal 12HL and hereinbelow will be referred to as an electrode terminal 12HLB. Reference numerals 14A and 14B correspond to the through electrode 14 (through-hole interconnection) and hereinbelow will be referred to as through electrodes 14A and 14B.

As shown in FIG. 4A, the external conductor terminal 12JA is electrically connected to the through electrode 14A. Similarly, the external conductor terminal 12JB is electrically connected to the through electrode 14B. Furthermore, the center conductor terminal 12IA is electrically connected to the electrode terminal 12HUA. Similarly, the center conductor terminal 12IB is electrically connected to the electrode terminal 12HUB.

The external conductor terminals 12JA and 12JB, the center conductor terminals 12IA and 12IB, and the electrode terminals 12HUA and 12HUB can be collectively formed by patterning using a known photolithographic technique or the like.

As shown in FIG. 4B, the through electrode 14A is electrically connected to the electrode terminal 12HLA. Similarly, the through electrode 14B is electrically connected to the electrode terminal 12HLB. That is, the external conductor terminal 12JA formed on the upper face 11U is electrically connected to the electrode terminal 12HLA formed on the lower face 11L with the through electrode 14A interposed therebetween. Moreover, the external conductor terminal 12JB formed on the upper face 11U is electrically connected to the electrode terminal 12HLB formed on the lower face 11L with the through electrode 14B interposed therebetween.

The electrode terminals 12HLA and 12HLB can be collectively formed by patterning using a known photolithographic technique or the like.

Also, the through electrodes 14A and 14B can also be formed by a known method.

Next, an electrical connection structure of the first coaxial cable 30A and the second coaxial cable 30B with respect to the image-sensing device electrode 42 will be described.

As shown in FIGS. 1 and 4A, the center conductor 31A of the first coaxial cable 30A is electrically connected to the center conductor terminal 12IA via the solder 16. In addition, the center conductor 31B of the second coaxial cable 30B is electrically connected to the center conductor terminal 12IB via the solder 16.

Consequently, the center conductor 31A is connected to the image-sensing device electrode 42U (42UA) via the center conductor terminal 12IA and the electrode terminal 12HUA, and the center conductor 31B is connected to the image-sensing device electrode 42U (42UB) via the center conductor terminal 12IB and the electrode terminal 12HUB.

Here, the image-sensing device electrode 42UA is one electrode of two image-sensing device electrodes 42U, that is, an electrode connected to the center conductor 31A of the first coaxial cable 30A. The image-sensing device electrode 42UB is the other electrode of the two image-sensing device electrodes 42U, that is, an electrode connected to the center conductor 31B of the second coaxial cable 30B.

As shown in FIGS. 1, 4A, and 4B, the external conductor 33A of the first coaxial cable 30A is electrically connected to the external conductor terminal 12JA via the solder 17. Furthermore, the external conductor 33B of the second coaxial cable 30B is electrically connected to the external conductor terminal 12JB via the solder 17. The external conductor terminal 12JA passes through the through electrode 14A, reaches the lower face 11L, and is connected to the electrode terminal 12HLA. The external conductor terminal 12JB passes through the through electrode 14B, reaches the lower face 11L, and is connected to the electrode terminal 12HLB.

Therefore, the external conductor 33A is connected to the image-sensing device electrode 42L (42LA) via the external conductor terminal 12JA and the electrode terminal 12HLA, and the external conductor 33B is connected to the image-sensing device electrode 42L (42LB) via the external conductor terminal 12JB and the electrode terminal 12HLB. Here, the image-sensing device electrode 42LA is one electrode of two image-sensing device electrodes 42L, that is, an electrode connected to the external conductor 33A of the first coaxial cable 30A. The image-sensing device electrode 42LB is the other electrode of the two image-sensing device electrodes 42L, that is, an electrode connected to the external conductor 33B of the second coaxial cable 30B.

According to one or more embodiments of the invention, only on the upper face 11U of the first substrate main body 11, the center conductor 31 (31A, 31B) is connected to the center conductor terminal 12I (12IA, 12IB), and the external conductor 33 (33A, 33B) is connected to the external conductor terminal 12J (12JA, 12JB). Consequently, it is necessary to provide a center conductor and an external conductor on the lower face 11L, and it is possible to form an empty space above the lower face 11L. Furthermore, since a center conductor and an external conductor are not formed on both the upper face 11U and the lower face 11L, the inner end face 11F shown in FIG. 1 is exposed, and it is possible to form an empty space above the inner end face 11F.

In the case of applying the imaging module 1 having the above-described empty space to a catheter, it is possible to achieve a catheter including a channel utilizing the empty space.

A catheter including the imaging module 1 will be described later.

In other cases, even where a sufficient empty space is present above the lower face 11L of the first substrate main body 11, a capacitor (bypass capacitor) may be provided between the electrode terminal 12HLA and the electrode terminal 12HLB.

Additionally, a resin mold may be formed on the upper face 11U of the first substrate main body 11 so as to coat the solder 15, 16, and 17, the center conductor 31 and the external conductor 33 of the signal cable 30, and the upper face resists 13A and 13B. By forming the resin mold on the upper face 11U as stated above, it is possible to increase the strength of the first substrate main body 11.

Moreover, when a sufficient empty space is present above the lower face 11L of the first substrate main body 11, a resin mold may be formed on the lower face 11L so as to coat the solder 15 and the lower face resist 13C. By forming the resin mold on the lower face 11L as stated above, it is possible to increase the strength of the first substrate main body 11.

Furthermore, a resin mold may be formed on both surfaces of the first substrate main body 11. In this case, it is possible to further increase the strength of the first substrate main body 11 by the resin mold formed on both surfaces.

Additionally, in one or more embodiments of the invention, the first wiring 12 (external conductor terminal, center conductor terminal, and electrode terminal) has the configuration in which a wiring pattern having two lines that linearly extend straight in the extending direction of the first substrate main body 11 is formed on each of the upper face 11U and the lower face 11L; however, the invention is not limited to the above-described linear wiring pattern. The first wiring 12 may has a cross pattern such that the first line of the wiring provided on the upper face 11U is connected to the second line of the wiring provided on the lower face 11L and the second line of the wiring provided on the upper face 11U is connected to the first line of the wiring provided on the lower face 11L.

Figure 5:
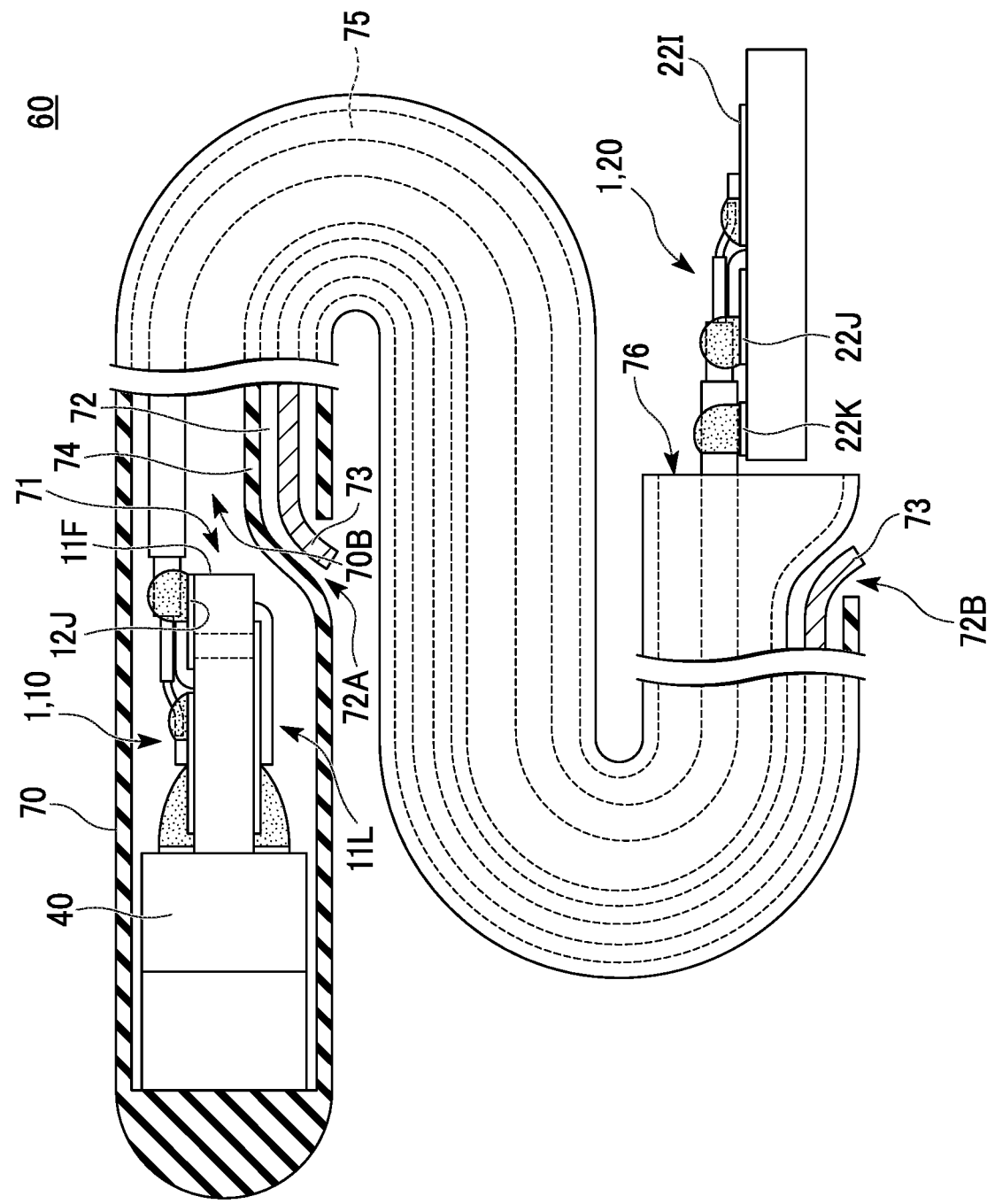
FIG. 5 is a partial cross-sectional view showing a schematic configuration of a catheter according to one or more embodiments of the invention.

FIG. 5 is a partial cross-sectional view showing a schematic configuration of a catheter 60 according to one or more embodiments of the invention.

In FIG. 5, identical reference numerals are used for the elements that are identical to those of the above-mentioned one or more embodiments of the invention, and the explanations thereof are omitted or simplified here. The catheter 60 shown in FIG. 5 is an imaging-module-attached catheter including the above-mentioned imaging module 1.

In the following explanation regarding the catheter 60, the position at which the solid-state image sensing device 40 or the first substrate 10 is disposed may be referred to as a front side, and the position at which the second substrate 20 is disposed may be referred to as a rear side.

The catheter 60 includes a tube 70 that is made of, for example, silicon or the like and has an insulation property. In one or more embodiments of the invention, silicon is adopted as a material used to form the tube 70, a flexible material or a metal material other than silicon may be used.

For example, as a flexible material, silicon, polyurethane, polyethylene, polytetrafluoroethylene (PTFE, for example, Teflon (registered trademark)), or the like is adopted. As a metal material, titanium, a titanium alloy, a stainless steel, or the like is adopted. Additionally, it is not limited to a flexible material or a metal material, and ceramic material may be used as a material used to form the tube 70.

The tube 70 includes a module insertion opening (not shown in the figure) located in front of the tube 70, a cable insertion opening 70B, a module arrangement region 71 in which the first substrate 10 and part of the signal cable 30 which form the imaging module 1 are disposed, a channel 72, a cable arrangement region 75, and a second substrate output port 76.

Specifically, in a step of manufacturing the catheter 60, the module insertion opening is an opening through which the imaging module 1 is inserted into the tube 70, the cable insertion opening 70B is an opening into which the second substrate 20 and the signal cable 30 which form the imaging module 1 are inserted, the cable arrangement region 75 is a tube through which the second substrate 20 passes, and the second substrate output port 76 is an opening through which the second substrate 20 is extracted from the tube 70.

The manufacturing steps described above are carried out, as a result, the solid-state image sensing device 40 is attached to the front of the tube 70 (the position close to (module insertion opening), the first substrate 10 and part of the signal cable 30 are disposed in the module arrangement region 71, the signal cable 30 is disposed in the cable arrangement region 75, and the second substrate 20 is disposed outside the second substrate output port 76.

The tube 70 has a front opening 72A located close to the first substrate 10 and a rear opening 72B located close to the second substrate 20, and the pathway formed between the front opening 72A and the rear opening 72B is the channel 72. The channel 72 is located between the external conductor terminal 12J (first cable terminal) and the external conductor terminal 22J (second cable terminal) and is disposed adjacent to the module arrangement region 71. The channel 72 is isolated from the module arrangement region 71 by an inner wall 74. The channel 72 is disposed within an outline of the solid-state image sensing device 40 on a plane of projection as seen in a direction from the solid-state image sensing device 40 to the inner end face 11F.

In other cases, the channel 72 may be used as a lumen and may be used as a working channel. In the case of using the channel 72 as a lumen, for example, a solvent medium injection lumen that ejects a solvent medium toward the front of the catheter 60 or a vacuuming lumen that removes liquid present in front of the catheter 60 can be provided in the tube 70.

Additionally, in the case of using the channel 72 as the working channel, for example, a treatment tool indicated by reference numeral 73 may be inserted into the channel 72. As the treatment tool 73, for example, various forcipes, a snare, a guide wire, a stent, a laser treatment tool, a high-frequency treatment tool, or the like is adopted.

In one or more embodiments of the invention, the channel 72 is formed by utilizing the empty space of the imaging module 1 in which the signal cable 30 is not provided. As described above, in the imaging module 1, it is not necessary to provide a center conductor and an external conductor on the lower face 11L, and the empty space is formed above the lower face 11L. Furthermore, the inner end face 11F is exposed, and the empty space is formed above the inner end face 11F. The channel 72 is provided by utilizing the above-described empty space.

According to one or more embodiments of the invention, as a result of using the empty space formed above the lower face 11L or the empty space formed above the inner end face 11F, it is possible to provide the channel 72 in the tube 70. Accordingly, the outer diameter of the catheter 60 does not increase in order to form the channel 72. It is possible to achieve the catheter 60 that includes both the channel and the imaging module and has a small diameter.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An imaging module comprising:
   an image-sensing device comprising an image-sensing device electrode;
   a first substrate comprising:
      a first insulating substrate main body comprising a plurality of surfaces;
      a first wiring disposed on the first insulating substrate main body;
      an electrode terminal electrically connected to the image-sensing device electrode and the first wiring; and
      a first cable terminal disposed on only one of the plurality of surfaces of the first insulating substrate main body, and electrically connected to the first wiring, wherein
      an end face of the first substrate is connected to the image-sensing device;
   a second substrate comprising:
      a second insulating substrate main body comprising a plurality of surfaces;
      a second wiring disposed on the second insulating substrate main body; and
      a second cable terminal disposed on only one of the plurality of surfaces of the second insulating substrate main body, and electrically connected to the second wiring; and
   a signal cable disposed between the first substrate and the second substrate and that electrically connects the first cable terminal to the second cable terminal,
   wherein when the first substrate and the second substrate are placed on a same horizontal plane, the one of the plurality of surfaces of the first insulating substrate main body where the first cable terminal is connected to a first terminal end of the signal cable and the one of the plurality of surfaces of the second insulating substrate main body where the second cable terminal is connected to a second terminal end of the signal cable are disposed on a same plane.

2. The imaging module according to claim 1, wherein the image-sensing device electrode is disposed on an electrode surface of the image-sensing device, and the first substrate is connected to the electrode surface so that an end face of the first insulating substrate main body is disposed between two of the image-sensing device electrode.

3. The imaging module according to claim 1, wherein the first substrate comprises:
   a first surface;
   a second surface opposite to the first surface; and
   a through electrode that penetrates through the first insulating substrate main body between the first surface and the second surface, and the first wiring is disposed on the first surface and the second surface and is electrically connected to the through electrode.

4. The imaging module according to claim 1, wherein the signal cable is a coaxial cable.

5. An imaging-module-attached catheter comprising:
the imaging module according to claim 1; and
a tube comprising:
- a module arrangement region where the first substrate and a portion of the signal cable are arranged; and
- a channel disposed between the first cable terminal and the second cable terminal and next to the module arrangement region,
- wherein, in a view from the image-sensing device, the channel is disposed within an outline of the image-sensing device on a plane of projection.

6. The imaging module according to claim 5, wherein
the first substrate is disposed in the module arrangement region in a distal end portion of the tube,
at least part of the signal cable is disposed in the channel, and
the second substrate is disposed outside a substrate output port that is disposed at a proximal end portion side of the tube.

* * * * *